United States Patent [19]

McMahon et al.

[11] 4,099,875

[45] Jul. 11, 1978

[54] COAXIAL MULTI-DETECTOR SYSTEM AND METHOD FOR MEASURING THE EXTINCTION COEFFICIENT OF AN ATMOSPHERIC SCATTERING MEDIUM

[75] Inventors: Donald H. McMahon, Carlisle; James B. Thaxter, Townsend, both of Mass.

[73] Assignee: Sperry Rand Corporation, New York, N.Y.

[21] Appl. No.: 766,473

[22] Filed: Feb. 7, 1977

[51] Int. Cl.² ............................................. G03B 27/10
[52] U.S. Cl. .................................... 356/103; 250/574
[58] Field of Search ................... 356/39, 102, 103, 104; 250/574

[56] References Cited

U.S. PATENT DOCUMENTS

3,519,354  7/1970  Brown .................................. 356/103
3,782,824  1/1974  Stoliar ................................. 356/103

Primary Examiner—Conrad J. Clark
Attorney, Agent, or Firm—Howard P. Terry

[57] ABSTRACT

An apparatus and method are provided for determining the extinction coefficient of an atmospheric scattering medium utilizing a single-ended optical system having a predetermined transmitter field of view and two concentrically arranged cooperating optical receivers, wherein backscattered light from near and far receiver fields of view for each of a series of transmitted light pulses is collected by the respective receivers. Optimum reception is achieved for both near and far field scatterers and the received signals are selectively processed by a processor which may include, for example, integration, summation, and differentiation steps that automatically yield extinction coefficient data under a wide range of environmental conditions without requirements of extreme apparatus stability, continuous monitoring, or calibration of the apparatus.

16 Claims, 10 Drawing Figures

COAXIAL MULTI-DETECTOR SYSTEM AND METHOD FOR MEASURING THE EXTINCTION COEFFICIENT OF AN ATMOSPHERIC SCATTERING MEDIUM

BACKGROUND OF THE INVENTION

1. Field of the Invention

The invention relates to optical apparatus and methods for measuring visibility through the atmosphere and is more particularly concerned with the measurement of the extinction coefficient of an atmospheric backscattering medium by techniques from which reliable measures can be achieved over a long atmospheric path through a variable density atmosphere.

2. Description of the Prior Art

Prior art concepts of interest with respect to the present invention are those of two United States patents:

U.S. Pat. No. 3,519,354 — R. T. Brown, R. F. Hazel, H. Laudon—"System for Measuring Extinction Coefficients in the Atmosphere Utilizing Backscattered Signals", issued July 7, 1970, and U.S. Pat. No. 3,782,824 — A. P. Stoliar, R. T. Brown—"Apparatus and Method for Measuring Extinction Coefficient of an Atmospheric Scattering Medium", issued Jan. 1, 1974;

both patents are assigned to Sperry Rand Corporation.

The Brown et al patent concerns a single-ended system for the optical measurement of meteorological visual range under atmospheric conditions such as those tending to restrict visibility along aircraft landing runways, the measurement being made in terms of certain characteristics of backscattered pulsed optical signals. Brown et al employ a monochromatic, slightly divergent light beam radiated by a pulse transmitting laser. A cooperating optical receiver having a similarly divergent field of view is spaced laterally from the optical transmitter so that its field of view overlaps most of the length of the radiated beam, the overlapped relation necessarily beginning at a predetermined distance from the laser emitting face. The backscattered light pulse energy is analyzed to compute an average atmospheric extinction coefficient associated with the medium within the field of view of the receiver.

In the improvement of the Stoliar et al patent, the side-by-side relation of the transmitter and receiver patterns is no longer used, and the apparatus is improved to eliminate the need for highly precise calibration and optical alignment and to assure more accurate measurements irrespective of the absorption, backscatter, composition, and homogeneity characteristics of the backscattering medium. The Stoliar et al device is a single-ended system that demonstrates the advantage of not being restricted to making measurements in a homogeneous medium, in that the medium no longer has to be such that its extinction coefficient is substantially constant over a comparatively long range.

The Stoliar et al device employs a monochromatic optical transmitter for transmitting a series of optical pulses in a slightly diverging beam along a common propagation path in the scattering medium whose extinction coefficient is to be measured. A receiver sharing the common propagation path and proximate the optical transmitter has a field of view coaxially aligned with that propagation path so as to overlap substantially the full length of the transmitter irradiation field. Accordingly, the receiver readily detects optical pulse energy backscattered from the scattering medium. First and second integrators, for example, receive first and second successively returned light pulses and the logarithm of the ratio of the amplitudes of these integrated signals is derived to determine the extinction coefficient. The arrangement of the Stoliar et al patent is a significant advance in the art because it minimizes parallax effects found in the Brown et al system; however, it does not fully eliminate the problem of nonoverlapping beams for scattering at very short ranges and other problems causing poor signal-to-noise characteristics tend to arise when a compromise configuration reducing the parallax problem is attempted, as will be further discussed.

SUMMARY OF THE INVENTION

According to the invention, apparatus is provided for measuring the extinction coefficient of atmospheric backscattering media, which apparatus includes a single-ended optical system having a pulsed transmitter with a predetermined narrow field of view. Two optical receivers, concentrically arranged with respect to the transmitter optical axis, receive backscattered light pulses from their respective near and far fields of view. One receiver views backscatterers in the far field, while the other views backscatterers in the near field where the far field receiver is inherently blind to the optical transmitter pulses. The near field receiver thus provides near field backscatter data not obtainable in prior art systems. Thus, optimum reception is afforded for both near and far field scatterers and extinction coefficients may be smoothly derived throughout a variable density atmospheric medium.

The signals received by the near and far field detectors are summed or are selectively processed by automatic integration, logarithmic summing, and differentiation apparatus and extinction coefficient data is thereby generated. The outputs of the two receivers are in effect adjusted for proper relative amplitudes and the processed output is switched from the near field receiver to the far field receiver for backscatterers in the far field as soon as both receiver outputs are equivalent.

DESCRIPTION OF THE PREFERRED EMBODIMENTS

GENERAL

The extinction coefficient discussed in the foregoing patents is an optical attenuation parameter describing all of the visible energy lost from an ideally parallel light beam as it propagates through a turbid medium. This loss is generally produced both by optical scattering and by absorption processes operating in the gases making up the atmosphere and also on solid and liquid particles normally found suspended in such a gas medium. Scattering losses predominate when fog is present in the medium. Because of the relative diameters of typical water droplets found in fog with respect to the wavelengths of visible light, Mie scattering then prevails.

Fog is a polydispersion of water droplets; a wide range of water particle sizes is then distributed throughout each volume of the atmospheric medium. As the scattering functions for water droplets are dependent on particle size, a polydispersion of water droplets exhibits scattering functions substantially dependent on the total range and frequency distribution of droplet sizes. However, a direct consequence of the size distribution of fog particles is an almost complete lack of over-all wavelength dependence of the scattering process in the visible and near infrared regions. Accordingly, an arbitrarily selected optical wavelength may be employed in the investigation of visibility along atmospheric paths using optical backscattering phenomenon.

Visibility measurement systems such as those of the foregoing patents have been constructed using laser sources of illumination because they readily supply the radiation in a narrow forward-directed beam having only slight divergence. Such an optical beam is desired because of the nature of available optical receivers. For example, the larger the solid angle from which the optical receiver can detect light, the greater the possibility of collecting interfering background optical noise relative to the desired backscattered signal and, thus, the poorer the over-all signal-to-noise performance of the receiver system. In addition, the monochromatic nature of conventional laser emission is further advantageous, permitting filtering of the backscattered energy just before it reaches the optical detector with a narrow pass band filter; thus, only light in the narrow frequency band of the laser transmitter is received by the optical detector.

Accordingly, it is seen that the signal-to-noise characteristic of an optical visibility measurement system such as those of the aforementioned patents is beneficially maximized by using a transmitted optical beam of the smallest possible divergence, by permitting the receiver detector to have a field of view correspondingly narrow, and by restricting the backscattered light reaching the receiver detector to substantially only the wavelength transmitted by the laser transmitter. For these reasons, only laser optical sources are practical as transmitters for use in successful visibility measurement systems.

PRIOR NON-CONCENTRIC SYSTEMS

Figure 1:
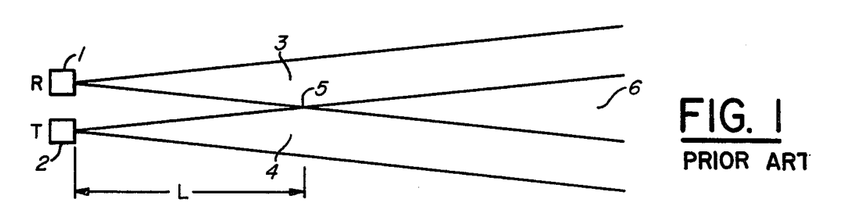
FIG. 1 is a plan view of the fields of view employed in non-concentric systems for the measurement of atmospheric extinction coefficients.
Figure 2:
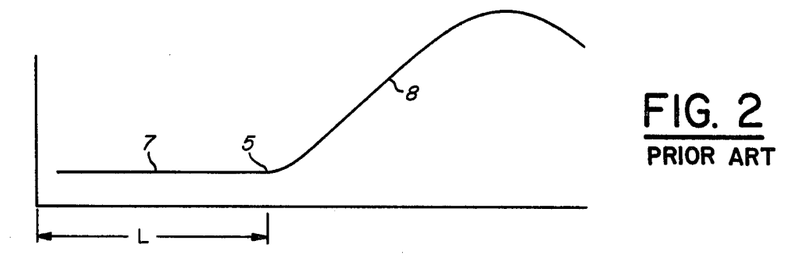
FIG. 2 is a graph useful in discussing the operation of the system of FIG. 1.

The optical transmitter and detector or receiver of the measurement system must be separated optically and electrically. In the Brown et al patent, such a separation is achieved in the non-concentric or side-by-side arrangement shown in FIG. 1 where is illustrated the overlapping region 6 of the transmitted beam supplied by the transmitter 2 and of the field of view 3 of receiver 1. Primary scattering elements in the atmospheric region 6 backscatter energy into receiver 1. On the other hand, primary scattering elements in the region of length L between the cross-over point 5 and the receiver 1 do not participate. That is, the off-set nature of the two fields causes them to be non-overlapping for scattering elements at a distance less than L. This is further complicated because of the possibility of a minor degree of secondary photon scattering by sets of two or more scattering elements residing in the fields. But neglecting such multiple scattering, as in the instance of relatively low fog densities, nearby scattering elements do not produce a srong backscatter signal in the non-concentric system, as shown by line 7 of FIG. 2. With this assumption, curve 8 begins to rise particularly at cross-over 5, since the number of primary scattering elements in overlapping region 6 increases with range. Absorption effects account for the subsequent peaking and falling off of the amplitude of curve 8. In the presence of increasing fog densities, multiple scattering effects become increasingly significant in the non-concentric or off-set system. In the usual circumstances in which moderate or low fog densities are of concern, there exists a particular distance, depending upon the movement of parallax and beam divergence in the Brown et al system, such that primary scattering elements nearer the laser emitter surface return weaker and weaker signals.

Accordingly, it is one object of the present invention to reduce significantly the undesirable weakening effect caused by the inherent geometry of the Brown et al system. Such an improvement may be accomplished by retaining certain features providing the greatly reduced parallex distance of the Stoliar et al coaxial receiver-transmitter visibility device, and by further beneficially modifying its structure and its signal processing system, as will be explained.

PRIOR CONCENTRIC SYSTEMS

Considering particularly the prior art Stoliar et al coaxial device, the light source and the optical receiver must again look at the same solid angle for distant scatterers. Because the light source and the optical receiver cannot be located at the same physical location, the coaxial arrangement uses a relatively short focal length lens for the light source and a relatively long focal length lens for the optical detector. The diameter of the collimating lens for the light source may be relatively small to produce a well-defined light beam and the lens is placed on the optical axis of the system. On the other hand, the receiver lens must collect a maximum backscattered signal and must therefore be large. Thus, in the Stoliar et al configuration, the receiver optical system concentrically surrounds the transmitter optical system. Optical isolation of the transmitted and received signals is effected by interposed light baffles.

Figure 3:
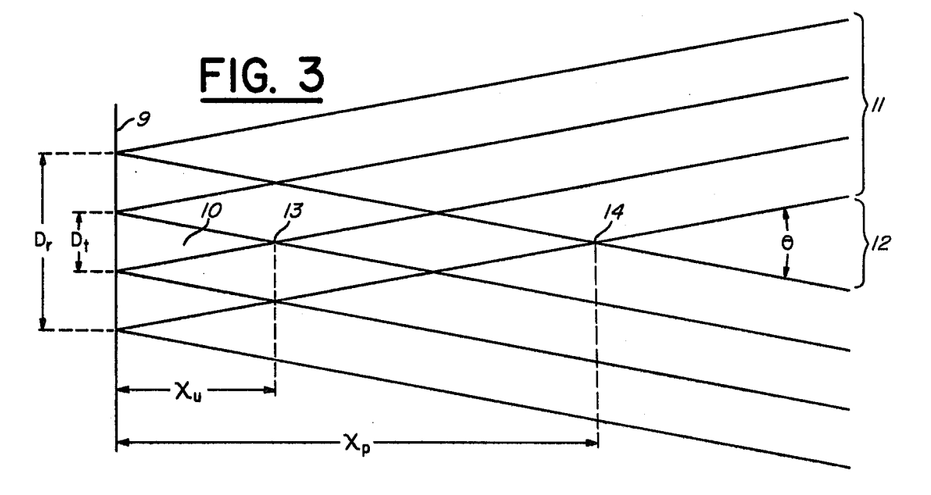
FIG. 3 is a plan view of the fields of view employed in a concentric system for measuring atmospheric extinction coefficients.

The zone geometry of the Stoliar et al coaxial system is shown in FIG. 3, where the plane 9 is the plane of the two objective lenses. It will be apparent from the inspection of FIG. 3 that the corresponding axial geometry minimizes parallax between the transmitter and receiver beams, but that it cannot eliminate the problem of non-overlapping beams for close scattering elements, this because of the presence of the total shadow umbra 10. Reference numeral 12 indicates an unshadowed beam region.

As indicated in FIG. 3, the central portion of diameter $D_t$ of plane 9 is reserved for the transmitter lens in the Stoliar et al device. The active area of the receiver objective lens is therefore restricted between an outer circle of diameter $D_r$ and the inner circle of diameter $D_t$. The spread or divergence angle $\theta$ of the receiver optical system is determined by the diameter of the light sensing area $d_r$ of the receiver and by the focal length $f_r$ of the receiver objective lens; that is:

$$\theta = d_r/f_r \quad (1)$$

From the values of $D_r$ and $D_t$, it may readily be shown that $x_u$, the axial length of the umbra shadow 10, is:

$$x_u = D_t/\theta = D_t f_r/d_r \quad (2)$$

and that $x_p$, the distance to the penumbra shadow 12, is:

$$x_p = D_r f_r/d_r \quad (3)$$

For a typical example, $f_r = 30$ inches and $d_r = 0.1$ inches; then, $x_u = 200$ feet, $x_p = 500$ feet, and $\theta = 3.3$ milliradians. Because an optimum signal-to-noise ratio is achieved when the divergence angles of the two beams are equal, the optimum ratio will occur in this example if the transmitter beam divergence angle is also 3.3 milliradians. Should the angular spread or divergence of the received field deliberately be made larger to reduce the umbra and penumbra distances $x_u$ and $x_p$, this reduction is made at the expense of a poorer signal-to-noise ratio for the system. It will be appreciated that the angle sizes in FIGS. 1 and 3 have been greatly exaggerated merely for the purpose of clarity in the drawings.

Another approach representing a modification of the Stoliar et al coaxial system entirely eliminates the parallax problem but introduces other objectionable difficulties. For example, a coaxial geometry may be employed in which a low-loss beam splitter is employed at an angle to the optical axis whereby separated routes from the transmitter and to the physically separated receiver are achieved, while still permitting exact overlapping of the beams in both the near and far fields. On the other hand, as much as half of the transmitted light is lost in transversing the beam splitter and half of the received backscattered signal is lost by reflection off the incident face of the beam splitter, causing an over-all 6 dB loss of the received signal. It will be appreciated that the effective range of the system would thereby be cut in half for a predetermined receiver objective lens diameter.

THE NEW CONCENTRIC SYSTEM

According to the present invention, an improved single-ended optical system is provided that achieves optimum signal-to-noise ratio characteristics for far field scatterers as well as for near field scatterers and, at the same time, eliminates the parallax problem for near field scatterers. The preferred geometry uses two separated light detectors and eliminates the 6 dB signal loss inherent in the beam splitter approach. One optical detector is tailored to receive light from a solid angle substantially equal to that of the transmitted beam. This optical detector is used to detect scattering elements in the far field of the system and is therefore optically isolated from the transmitter. A second optical detector is employed to eliminate the prior art signal loss in the near field caused by the parallax problem. This second optical detector shares use of the transmitter objective lens and occupies an area in the focal plane of the transmitter objective lens surrounding the optical transmitter source. The novel system thus determines the extinction coefficient along a line of sight, measuring meteorological characteristics in the near field as well as farther into the atmosphere.

Figure 4:
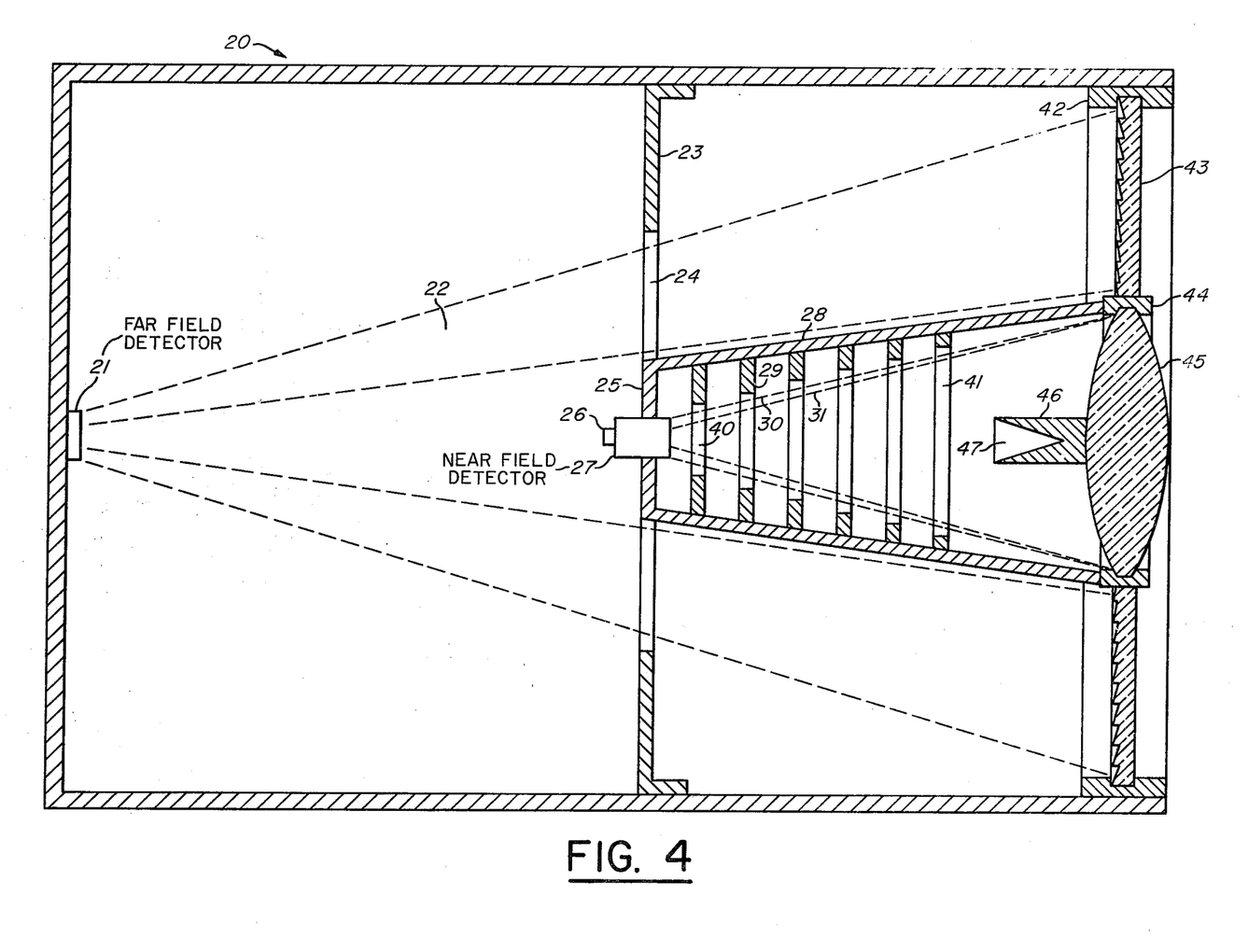
FIG. 4 is an elevation view in cross-section of the concentric optical system of the present invention.

In the novel dual-detector concentric measurement system shown in FIG. 4, light-proof casing 20 encloses and supports the near and far field optical systems including the near field detector 27 and far field detector 21. The near field optical system is shared by pulsed laser transmitter 26 and near field detector 27 arranged concentrically about it, elements 26 and 27 being disposed in a support 23 fastened within casing 20 in a conventional manner. Support 23 may have a conventional spider configuration with thin radial support arms, such as arm 24, joining the circular support portion 25 to casing 20 so that the arms intercept minimum light. The near field detector 27 and laser transmitter 26 have their own separated optical space shielded internally of a frustrated conical shield 28 supported within arms 24 and at inner retaining ring 44 by lens 43 and at outer retaining ring 42 disposed within casing 20. Within conical shield 28 is a series of apertured light baffles, such as baffle 29, the series having apertures which increase in size from aperture 40 to aperture 41 so as to pass all light within the conical outer locus 30 of the backscattered light pattern flowing through lens 45 to annular near field detector 27. Lens 45 is disposed in a conventional manner within lens retainer 44 and, along its axis, supports a light absorber 46 having a reentrant conical portion 47. Light absorber 46 prevents reflection of light from laser transmitter 26 off the relatively flat central inner portion of lens 45 into the annular near field detector 27. Light from transmitter 26 flows withing the confines of locus 31 to illuminate lens 45.

The second or far field detector 21 also lies on the axis of the total system; it receives backscattered light collected by annular Fresnel lens 43 which focusses the received light so that it flows in an annular beam 22 into far field detector 21. The hollow light beam is annular because of the annular nature of the conventional Fresnel lens 43 and its accommodation of the near field optical system. Fresnel lens 43 has a focal length selected so that the divergence angle of far field receiver 21 matches that of the transmitter beam so as to optimize the signal-to-noise ratio for large range backscatterers. The support system 23 forms a baffle, permitting annular beam 22 to flow through it in the region of support arms 24.

It will be understood that near field detector 27 cannot occupy the same physical space as light source 26; as a consequence, near field detector 27 cannot receive light from primary scattering elements in the far field because such scattering elements may return light only to the area occupied by the radiating face of transmitter 26. Accordingly, the near field or transmitter focal plane detector 27 is restricted to viewing only light from scattering elements in the near field.

Because the transmitter focal plane detector 27 accepts light backscattered only from the near field, and the isolated coaxial detector 21 accepts only light backscattered from the far field, the relative detector-optical geometry is adjusted to provide a smooth transition between the near and far field detectors. This is accomplished by arranging the inner circumference of near field detector 27 to subtend substantially the same solid angle as the outer diameter of far field light detector 21. Because near field detector 27 inherently has a wider angle of view than the transmitter beam, the dimension of the outer diameter of far field detector 21 is not particularly critical; on the other hand, for best signal-to-noise characteristics, that outer diameter should be as small as possible. The theoretically ideal near field detector 27 is therefore a narrow ring centered on laser transmitter 26 with an inner diameter equal to the outer diameter of the laser source.

The proximity of near field light detector 27 to laser source 26 and the ring shape of the sensitive area of detector 27 require that light-collimating elements be interposed essentially to convert the necessary ring shaped receiver area to a shape compatible with the active surface of the single conventional light detector unit 26. The fiber optic system of FIGS. 5 and 6 serves this purpose, as will be explained. Near field detector 27 need not be as sensitive as far field detector 21 because of the greater strength of the signal backscattered by nearly scattering elements. However, near field detector 27 shares the same objective lens 45 as is used by laser transmitter 26, so that the baffles 29 and the axial absorber 46 are used to improve optical isolation between transmitter 26 and detector 27. It will be understood that absorber 46 may be replaced simply by an axial bore through lens 45.

Figures 5, 6:
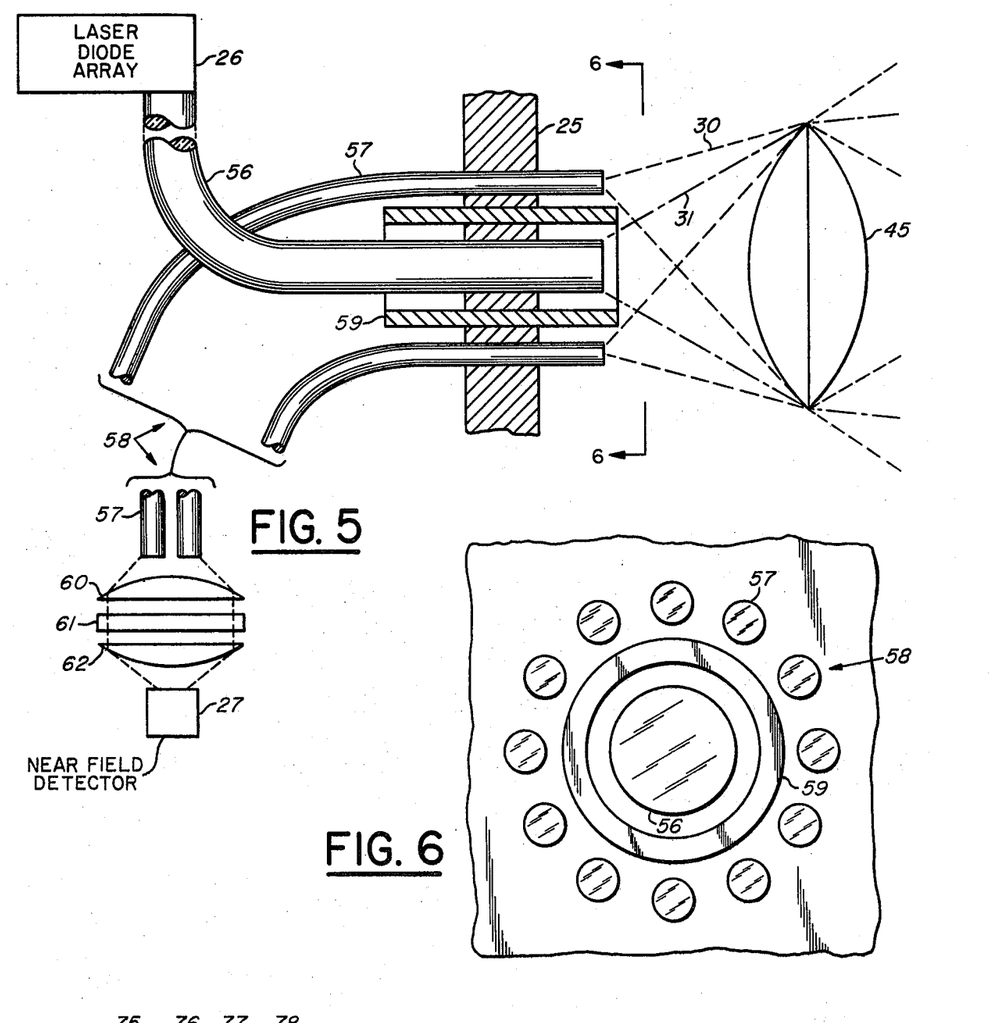
FIG. 5 is an elevation view, partly in cross-section, of the transmitter and near field detector portions of FIG. 4.
FIG. 6 is a fragmentary plan view taken along the line 6—6 of FIG. 5.

FIGS. 5 and 6 illustrate a preferred form of transmitter 26 and the concentric annular detector 27 of FIG. 4. A conventional pulsed laser diode array 26 is coupled in a conventional manner to a single optical waveguide 56 having a remote end supported along the optical axis of the system by support wall 25. Alternatively, guide 56 may constitute a bundle of fiber optic guides. The optical beam radiated by the emitter face of optical waveguide 56 forms the diverging beam 31 which illuminates lens 45. Near field reception is accomplished by a circular array 58 of optical waveguides, such as optical fiber 57, coupled to the annular receiver pattern 30 formed by the same centrally located glass objective lens 45. Waveguide array 58 concentrically surrounds transmitter guide 56 or guides, though they are separated by hollow cylindric shield 59 used to avoid direct coupling of the receiver and transmitter systems. Elements 57, 58, and 59 may all be conveniently mounted within support wall 25. Array 58 is coupled to near field detector 27 by suitable lenses 60 and 62, a filter 61 also being included in the light path. Filter 61 preferably passes only the narrow band of frequencies generated by laser array 26. Laser array 26 and near field detector 27 and associated lenses 60, 62, because of the beneficial nature of the fiber optical waveguides, are advantageously located in casing 20 but outside of the region required for propagation of the annular backscattered beam 22.

A suitable power supply and pulse shaping circuits, amplifiers, and modulator circuits (none shown) may be included in the conventional manner within the package of the laser diode array 26, as well as a conventional temperature control system (not shown) for the lasers themselves. If required, a plurality of conventional single heterojunction GaAs laser diodes may readily be employed as a transmitter array, yielding a one kilowatt output at 9100 Angstroms at a repetition rate of about 5 kHz, for example. The role of the near field optical detector 27 seen in detail in FIGS. 5 and 6 may readily be taken by a conventional silicon diffused p-i-n photodiode with the usual associated amplifier circuits. The conventional filter 61 may be centered at 9100 Angstroms with about a 200 Angstrom pass band.

Figure 7:
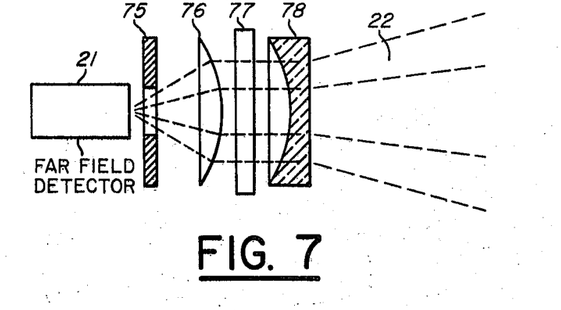
FIG. 7 is a plan view of the far field detector portion of FIG. 4.

The far field detector shown in FIGS. 4 and 7 employs, as a receiving lens, the Fresnel lens 43 with its central portion removed to accommodate near field detector-transmitter lens 45. Lenses 76, 78 are used to focus pattern 22 on the active face of a conventional silicon avalanche photo-diode, with a filter 77 generally like filter 61 being placed between lenses 76, 78. An adjustable stop 75 is placed immediately in front of the photodiode and is used in matching the spread angle of the transmitter and receiver beams. The optical elements 75, 78 are used in the usual way to assure that received light will normally be incident upon the face of interference filter 77, lenses 76 and 78 being respectively positive and negative. It will be understood by those skilled in the art that casing 20 of the apparatus will normally be arranged for manual rotation about vertical and horizontal axes, as on a conventional stable tripod equipped, if desired, with azimuth and elevation angle output decoders and that suitable methods for levelling the tripod will be provided in practical usage of the system.

THE NOVEL PROCESSING SYSTEM

Figure 8:
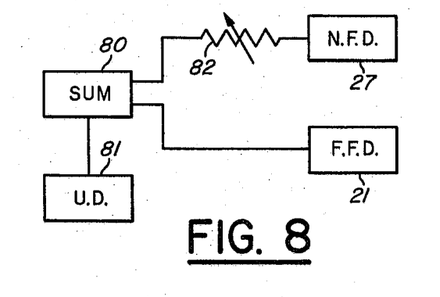
FIG. 8 illustrates one alternative circuit for utilizing the outputs of the receivers of FIG. 4.

To make effective use of the novel visibility measurement system, signals derived by far and near field detectors 21, 27 must be processed. Under limited circumstances, simple direct addition (FIG. 8) in a summing circuit 80 of the outputs of detectors 21, 27 may be employed. Such simple addition of the electric signals, appropriately adjusted by attenuator 82, to make their relative amplitudes equal, is useful but is not, however, a generally optimum approach because the resultant noise level in the output of summing circuit 80 is the sum of noise signals present in the outputs of the respective preamplifiers within receivers 21, 27. In particular, if the near field detector 27 is not as sensitive as the far field detector, which would be the case if a least expensive detector were used for viewing the near field, the near field detector 27 output signal must be amplified more than the output of far field detector output signals of substantially the same level, especially in the transition region between the near and far fields. In such a circumstance, near field detector 27 would contribute a noise component for scattering elements at large distances far greater than the noise component from far field detector 21. According to the present invention, the respective signal outputs of detectors 21, 27 will be adjusted for proper relative amplitudes, but the processor imput must be switched between the output of the near field detector 27 and the far field detector 21 as a means of minimizing effects of the near field noise level. According to one embodiment of the invention, switching from near field detector 27 to far field detector 21 uses calculation of the beam attenuation separately using each detector and then switching the utilization device 81 from the near field signal to the far field signal as soon as both detectors yield equivalent signal levels.

Figure 9:
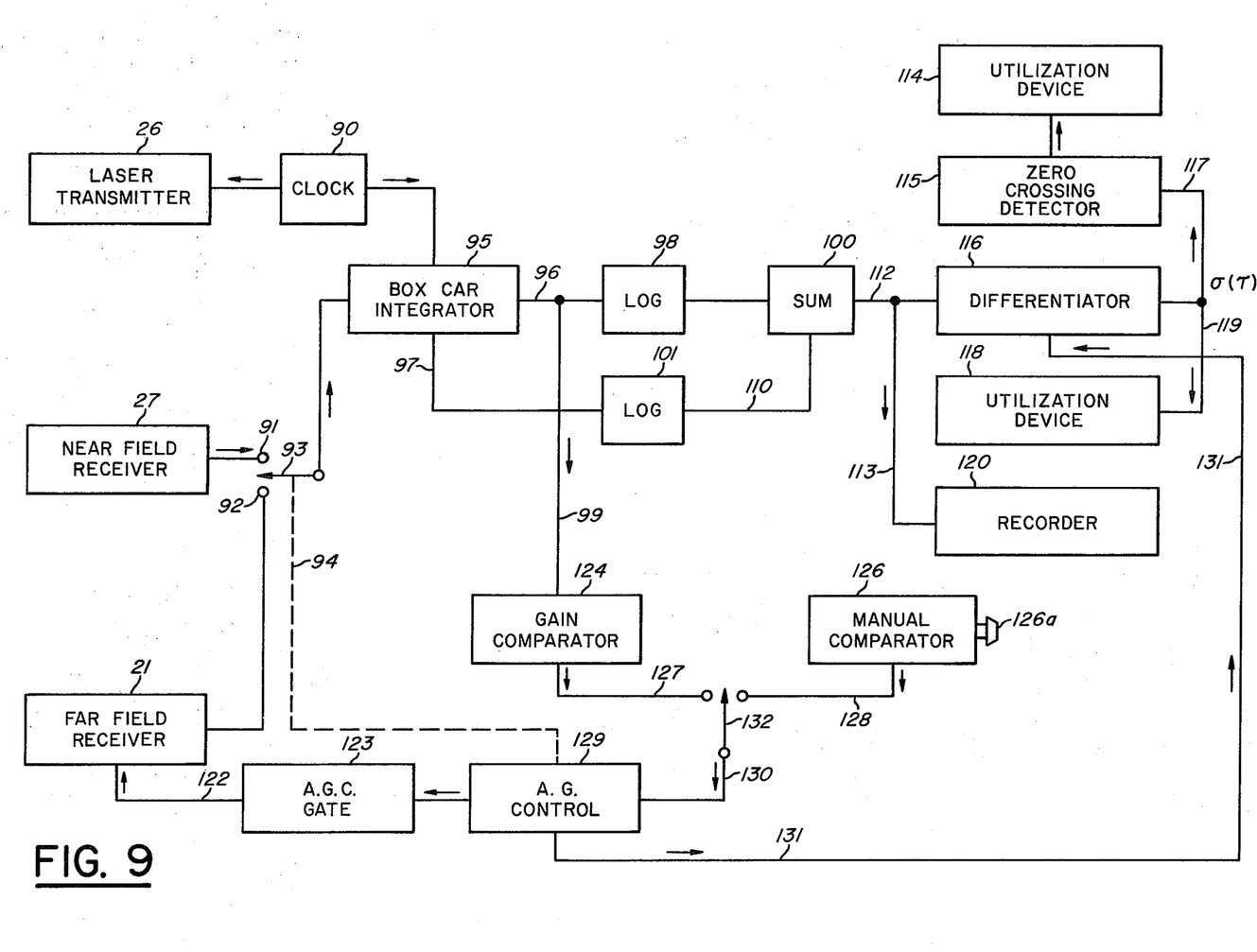
FIG. 9 illustrates a preferred form of the circuit for processing the outputs of the receivers of FIG. 4.

In FIG. 9, the novel signal processor system is synchronized by a conventional clock or pulse synchronizer 90 which also determines the pulse repetition rate of laser transmitter 26. The respective near and far field detectors 27 and 21 are coupled to terminals of switch 93, whereby they are selectively coupled to the input of a conventional box car integrator 95. The latter supplies discrete averaged and stretched pulse outputs on lead 96 with improved signal-to-noise ratio; the lead 96 output is coupled into a conventional logarithmic circuit 98, whose output is supplied to one input of summation circuit 100 whose output, in turn, is coupled via lead 112 to differentiator 116 and via branching lead 113 to a conventional recorder 120.

A sweep output of the conventional box car integrator 95 is coupled by lead 97 to a second conventional logarithmic circuit 101. The logarithmic output of circuit 101 is coupled via lead 110 as a second input to sum circuit 100. The total output of summation circuit 100 is coupled via lead 112 to differentiator 116, whose output is coupled via lead 119 to utilization device 118, which latter may be a conventional display having a numerical read-out, and is further coupled via branching lead 117 to conventional zero-crossing detector 115 for supply to a second utilization device 114, which may also be a conventional display with a numerical read-out.

For control of the gain of far field receiver 21 and also for selective operation of switch 93, a lead 99 branching from the output lead 96 of box car integrator 95 supplies a control signal to gain comparator 124. Manually settable gain control 126 may alternatively be used according to the setting of selector switch 132. One or the other of the respective comparators 124, 126 couples a control signal via lead 130 to automatic gain controller 129. Controller 129 has three functions according to its input on lead 130. First, it controls a conventional automatic gate circuit 123 to supply a signal via lead 122 for selecting one of two values for the gain of far field receiver 21. Through a mechanical connection 94 which may include a suitable relay solenoid, control 129 selectively positions switch 93; it will be understood that a semiconductor or other electronic switch may be similarly controlled as a substitute for mechanical switch 93. Finally, via lead 131, automatic gain control 129 controls differentiator 116, as will be further described.

The output of box car integrator 95 is a modified replica of its input wave form, amplified, considerably stretched from its original length, and with noise significantly suppressed so that it is in good form for extraction of the extinction coefficient $\sigma$ by the mechanism disclosed in FIG. 9. To understand the operation of this mechanism, consideration of the following theoretical treatment based generally upon the discussion of the aforementioned Stoliar et al U.S. Pat. No. 3,782,824 will be useful. Considering the propagation of a single transmitted pulse in the novel coaxial system, backscattered radiation is continuously received as the forward propagating light pulse continuously encounters successive scatterers. The received backscattered radiation decreases in intensity as a function of travel time of the light pulse both according to inverse square losses and to exponential decay losses produced by scattering and absorption as extinction factors. At any one instant of pulse travel time (or at any one range), the magnitude of the detected backscattered radiation is well known to be:

$$P_R(r) = \frac{P_T s A_e}{8\pi} \frac{\beta_\pi(r)}{r^2} \exp -2\int_0^r \sigma(x)dx \quad (4)$$

where:
$P_R(r)$ = received power from scatterer at range $r$,
$P_T$ = transmitted power,
$s$ = transmitted pulse length,
$A_e$ = effective receiver aperture, $\beta_\pi(r)$ = volume backscatter coefficient at range $r$,
$\sigma(r)$ = extinction coefficient at range $r$, and
$r$ = atmospheric range of the light scatterer.

In equation (4), range-dependednt and range-independent factors have been separated, so that taking the logarithm of both sides of equation (4) yields:

$$\log P_R(r) = \log K - 2\log r + \log \beta_\pi(r) - 2\int_0^r \sigma(x)dx \quad (5)$$

where the quantity $P_T s A_e/8\pi$, not being dependent on $r$, has been replaced simply by the constant K.

To derive the components in the right hand side of equation (5), $2 \log r$ is computed by logarithmic circuit 101. The instantaneous range $r$ required for this term is simply derived from the conventional sweep voltage output on lead 97 of box car integrator 95. This sweep has a period relatively long compared to the repetition interval of clock 90, being about 15 seconds long, for example. The logarithmic circuit 101 supplies $2 \log r$ over lead 110 to be algebraically summed with the output of logarithmic circuit 98.

Now, differentiation of equation (5) with respect to time yields:

$$\frac{d}{dt}(\log P_R(r)) = \frac{1}{\beta_\pi(r)} \frac{d\beta_\pi(r)}{dr} - 2\sigma(r)\frac{dr}{dt} \quad (6)$$

In the usual situation, the $\beta_\pi(r)$ term varies only slowly with range $r$; thus the term $$\frac{1}{\beta_\pi(r)} \frac{d\beta_\pi(r)}{dr}$$

can be neglected with respect to $2\sigma(r)$. In this manner, the output of differentiator 116 is substantially directly proportional to $\sigma(r)$ which is desired data.

The output of box car integrator 95 is monitored via lead 99 by the conventional gain comparator 124. This circuit supplies an output level proportional to the received backscattered signal power $P_R(r)$ with respect to a reference, which output may be coupled via lead 127, switch 132, and lead 130 to a.g. control 129. Control 129, though conventional, is of a special kind providing an output at one of two spaced levels in the presence of an input. If the signal on lead 130 rises above an upper threshold level, a.g. control 129 commands a.g.c. gate 123 to supply a reduced bias voltage to the photodiode of far field detector 21, thus reducing the photodiode gain. On the other hand, if the output voltage on lead 130 drops below a lower threshold level spaced apart from the upper threshold level, a.g. control 129 commands gate 123 to increase the gain of the photodiode. The two threshold levels are used to afford the required dynamic range for the system without hunting. The photodiode of far field receiver 21 has a rapid response time, so that little data is affected because of gain changes in view of the relatively long sweep time of box car integrator 95.

With switch 130 coupled to output lead 127 of gain comparator 124, the gain comparator output ultimately causes switch 93 to move from terminal 92 to terminal 91, thus connecting near field receiver 27 to the input of box car integrator 95, and disconnecting far field receiver 21, as has previously been discussed. Control 129 operates switch 93 in a few milliseconds, so that the switching event may act on box car integrator 95 as if a sudden gain change had occurred. The manually set comparator 126 may be used in place of automatic comparator 124, if gain range switching is desired at manually selectable times during the box car integrator 95 sweep, by moving switch 132 to contact lead 128.

Figure 10:
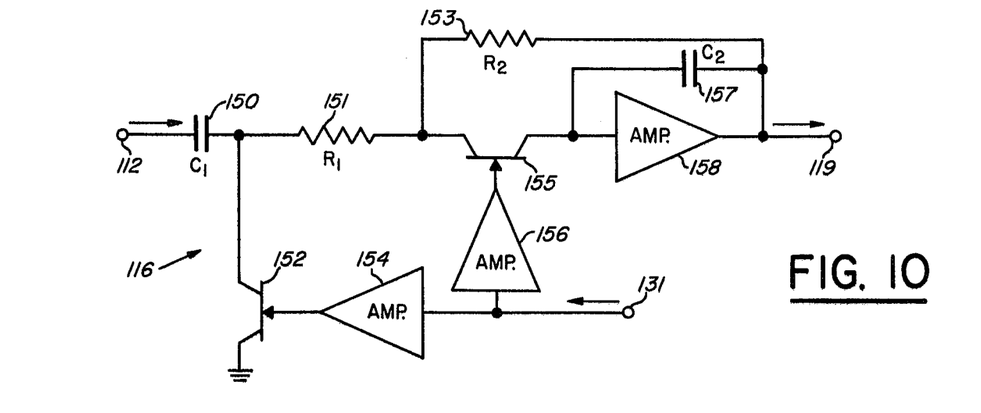
FIG. 10 is a detailed drawing of the differentiator circuit of FIG. 9.

Actual gain changes produced by operation of a.g.c. gate 123 or effective gain changes caused by the operation of switch 93 evidently may cause sudden undesired changes in the amplitude of the input to differentiator circuit 116 which should not be allowed to affect the differentiated output on leads 117, 119; the circuit of FIG. 10 prevents the undesired result. Output lead 112 of sum circuit 100 is coupled by capacitor 150 through resistor 151 and through field effect transistor 155 and operational amplifier 158 to the output leads 117, 119 of differentiator 116. The output of operational amplifier 158 is coupled from lead 117 through capacitor 157 to the output side of transistor 155, while the same output is coupled through resistor 153 to the input side of transistor 155. The pairs of resistors and capacitors are selected according to the law $R_1C_1 = R_2C_2$. The two amplifiers 154, 156 are responsive to the dump signal from a.g.c. circuit 129 applied via lead 131. Amplifier 156 controls the conductivity of transistor 155 directly. Amplifier 154 controls the conductivity of a second field effect transistor 152 connected between ground and the junction between capacitor 150 and resistor 151.

The circuit of FIG. 10 operates as a band-limited differentiator. During an undesired abrupt gain change, capacitor 150 is connected to ground by the action of the dump pulse on lead 131, while the output on lead 117 is held substantially constant by capacitor 157. The differentiation time constant is $R_2C_2$; at frequencies above $(1/R_1C_1 = 1/R_2C_2)$ the gain rolls off at 6 dB per octave, for example, desirably reducing the effects of input noise, including switching transients.

The versatile processor system permits various uses to be made of its computed output. The output of sum circuit 100 or of differentiator 116 may be recorded in analog or in digital form on magnetic tape for further data processing or may be used directly in a conventional universal data processor. It will be understood by those skilled in the art that various quantities may easily be recorded, such as averaged backscattered power, its logarithm, the logarithm of range-corrected averaged backscattered power, or the extinction coefficient itself. The output of differentiator 116 feeding zero-crossing detector 115 provides a measure of the time-to-maximum-peak of the backscattered signal, which signal may be displayed by device 114 or similarly recorded.

While the invention has been described in analog form, it will be readily appreciated by those skilled in the art that all or portions of the functions of the analog computing elements of the invention as discolsed may be performed within the scope of the invention by substituted analogous digital computing elements.

While the invention has been described in its preferred embodiments, it is to be understood that the words which have been used are words of description rather than of limitation and that changes may be made without departing from the true scope and spirit of the invention in its broader aspects.

We claim:

1. In a system for determining the extinction coefficient of an atmospheric scattering medium, apparatus comprising:

transmitter means for irradiating the scattering medium whose extinction coefficient is to be determined with a series of pulses of radiation directed along a predetermined propagation path, near field receiver means responsive to radiation backscattered from first scattering elements disposed in the near field of view within said predetermined propagation path for producing a first receiver output, far field receiver means responsive to radiation backscattered from second scattering elements disposed in a far field of view concentric with said predetermined propagation path for producing a second receiver output, and processor means responsive to said first and second receiver outputs for providing a measure of the extinction coefficient for said atmospheric scattering medium with respect to both said first and said second scattering elements.

2. Apparatus as described in claim 1 further including:

first lens means having a first predetermined focal plane for said radiation,
   said transmitter means being disposed at said first predetermined focal plane, and
   said near field receiver means being disposed at said first focal plane in contiguous coaxial relation with respect to said transmitter means.

3. Apparatus as described in claim 2 further including:

second lens means having a second predetermined focal plane for said radiation spaced from said first predetermined focal plane opposite said first lens means,
   said far field receiver means being disposed at said second focal plane.

4. Apparatus as described in claim 3 wherein said second lens means comprises an annular lens having a hollow central region and is disposed in coaxial relation about said first lens means.

5. Apparatus as described in claim 4 including means for isolating the region between said first lens means and said transmitter means from the region between said second lens means and said far field receiver means.

6. Apparatus as described in claim 5 further including absorption means disposed at a central portion of said first lens means whereby radiation from said transmitter means is not reflected by said lens means into said near field receiver means.

7. Apparatus as described in claim 1 wherein:

said transmitter means comprises laser means providing radiation falling within a narrow band of optical frequencies, and
   said near and far field receiver means include filter means for passing substantially only said narrow band of optical frequencies.

8. Apparatus as described in claim 1 wherein said processor means includes:

attenuator means for adjusting the relative amplitudes of the outputs of said near and far field receiver means,
   summation means responsive to the adjusted relative-amplitude outputs of said summation means for producing a sum output, and
   utilization means responsive to said sum output.

9. Apparatus as described in claim 1 additionally including:

pulse synchronizer means, said transmitter means comprising pulsed laser means for generating pulses of optical radiation in response to said pulse synchronizer means.

10. Apparatus as described in claim 9 further including:
- integrator means responsive to said far field receiver means and synchronized by said pulse synchronizer means for producing stretched pulse and sweep output signals,
- first logarithmic circuit means responsive to said stretched pulse output signals,
- second logarithmic circuit means responsive to said sweep output signals,
- summation means responsive to said first and second logarithmic circuit means,
- differentiator means responsive to said summation means output for providing a measure of said extinction coefficient, and
- means for utilizing said measure.

11. Apparatus as described in claim 10 further including means for recording said summation means output.

12. Apparatus as described in claim 10 wherein said means for utilizing said measure includes numerical display means.

13. Apparatus as described in claim 10 wherein said means for utilizing said measure includes:
- zero-crossing detector means, and display means responsive to said zero-crossing detector means.

14. Apparatus as described in claim 10 further including:
- comparator means responsive to said stretched pulse output signal, and
- automatic gain control means responsive to said comparator means for selectively controlling the gain of said far field receiver between first and second predetermined gain levels.

15. Apparatus as described in claim 14 further including first switch means for selectively coupling said far field receiver or said near field receiver to said integrator means in response to said automatic gain control means.

16. Apparatus as described in claim 15 additionally including:
- second switch means for switching said summation means output from said differentiator means to ground in response to an abruptly changing output from said automatic gain control means,
- said differentiator means being of the band-limited type whereby the effects of noise and switching transients are substantially reduced.

* * * * *